(12) United States Patent
Ahmed

(10) Patent No.: US 6,861,411 B1
(45) Date of Patent: Mar. 1, 2005

(54) METHOD OF TREATING EYE INFECTIONS WITH AZITHROMYCIN

(75) Inventor: Imran Ahmed, East Lyme, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/200,119

(22) Filed: Nov. 25, 1998

Related U.S. Application Data

(60) Provisional application No. 60/067,250, filed on Dec. 2, 1997.

(51) Int. Cl.[7] ............................................. A61K 31/70
(52) U.S. Cl. ......................................... 514/29; 536/7.4
(58) Field of Search ............................. 514/29; 536/7.4, 536/7.3

(56) References Cited

U.S. PATENT DOCUMENTS

| | | | |
|---|---|---|---|
| 4,474,768 A | | 10/1984 | Bright |
| 4,512,982 A | * | 4/1985 | Hauske et al. ................. 514/29 |
| 4,551,456 A | | 11/1985 | Katz .......................... 514/254 |
| 4,692,454 A | | 9/1987 | Mich et al. .................. 514/312 |
| 4,851,415 A | | 7/1989 | Mich et al. .................. 514/278 |
| 5,250,518 A | | 10/1993 | Kobrehel et al. ............. 514/29 |
| 5,441,939 A | | 8/1995 | Yang ........................... 514/29 |
| 5,498,699 A | | 3/1996 | Djokic et al. ................. 534/15 |
| 5,605,889 A | | 2/1997 | Curatolo et al. .............. 514/29 |
| 5,631,004 A | | 5/1997 | Cagle et al. ............. 424/78.04 |
| 5,646,151 A | * | 7/1997 | Kruse et al. ................ 514/255 |

FOREIGN PATENT DOCUMENTS

| | | | |
|---|---|---|---|
| EP | 0126684 | 11/1984 | .......... A61K/47/00 |
| EP | 0142426 | 5/1985 | ......... A61K/31/495 |
| EP | 0298650 | 1/1989 | ........... C07H/17/02 |
| EP | 0445743 | 9/1991 | .......... A61K/31/71 |
| EP | 0467331 | 1/1992 | ........... C07H/17/08 |
| EP | 0677530 | 10/1995 | ........... C07H/17/08 |
| EP | 0679400 | 11/1995 | .......... A61K/31/71 |
| EP | 0879823 | 11/1998 | ........... C07H/17/08 |
| EP | 0925789 | 6/1999 | .......... A61K/31/70 |
| JP | 11240838 | 9/1999 | .......... A61K/31/70 |
| WO | WO8901772 | 3/1989 | ............ A61K/9/00 |
| WO | 9509601 | 4/1995 | ............ A61K/7/16 |
| WO | WO9509601 | 4/1995 | ............ A61K/7/16 |
| WO | 9619489 | 6/1996 | ........... C07H/17/08 |
| WO | 9620010 | 7/1996 | .......... A61K/45/06 |
| WO | WO9817280 | 4/1998 | .......... A61K/31/70 |

OTHER PUBLICATIONS

Robert E. Leonard II, Carol L. Karp, and Eduardo C. Alfonso, Erythromycin, Clarithromycin, and Azithromycin, 1997, Textbook of Ocular Pharmacology, pp. 515–523.
Robert H. Cross, Gary N. Holland, Samuel J. Elias and Rachel Tuz, Corneal Pharmacokinetics of Topical Clarithromycin, Apr. 1995, Investigative Ophthalmology & Visual Science, vol. 36, No. 5, pp. 965–968.
Citation 1: Ophthalmology, vol. 103, p. 842–846, 1996.
Citation 2: Merck Manual No. 16, (Yugengaisha), Medicial Book Service May 1, 1995, p. 2266–2267.
Citation 3: New Edition Diseases and Drugs, Kabushiki Kaisha Yakujinippousha, Jun. 15, 1986, p. 583–594.
Translation of pertinent passages of Citation 2.
Translation of pertinent passages of Citation 3.
First Meeting of the WHO Alliance For The Global Elimination of Trachoma, Geneva, Jun. 30–Jul. 1, 1997, Room A (Main Building).
Jaruratanasirikul, Sutep et al, "Distribution of azithromycin into brain tissue, cerebrospinal fluid, and aqueous humor of the eye", Antimicrob. Agents Chemother., 1996, 40, 825–6, XP002098516.
Bailey RI et al: "Randomised controlled trial of single–dose azithromycin in treatment of trachoma.", Lancet, Aug. 21, 1993, 342, p453–6, XP002098517.
Thylefors B. "Azithromycin A new opportunity for control of trachoma", Who Drug Informaion, 132–133, XP002098518.

\* cited by examiner

*Primary Examiner*—Elli Peselev
(74) *Attorney, Agent, or Firm*—Peter C. Richardson; Gregg C. Benson; Lance Y. Liu

(57) ABSTRACT

The invention features methods and compositions for treating ocular infections. The method comprises topically administering to an eye of an animal in need of such treatment an ocular infection-treating amount of azithromycin.

8 Claims, No Drawings

METHOD OF TREATING EYE INFECTIONS WITH AZITHROMYCIN

This application is filed claiming priority from Provisional Application No. 60/067,250 filed Dec. 2, 1997.

FIELD OF THE INVENTION

This invention relates to methods of treating eye infections by topically administering azithromycin to an eye of an animal in need of such treatment.

BACKGROUND OF THE INVENTION

Azithromycin is the U.S.A.N. (generic name) for 9a-aza-9a-methyl-9-deoxo-9a-homoerythromycin A, a broad spectrum antimicrobial compound derived from erythromycin A. Azithromycin is disclosed in U.S. Pat. No. 4,474,768 to Bright and U.S. Pat. No. 4,517,359 to Kobrehel et al. These patents disclose that azithromycin and certain derivatives thereof possess antibacterial properties and are accordingly useful as antibiotics.

Azithromycin is commonly administered orally, in a number of different dosage forms such as tablets, capsules, and suspensions, for the treatment of antibacterial infections. Until the present invention, however, azithromycin was not known to be effective when topically administered to the eye. Azithromycin is known to be effective for the treatment of eye infections in humans when administered systemically, e.g., orally. However, it is also known that antibiotics which are effective when administered by a systemic route are not necessarily effective when applied topically, directly to the eye. For example, it has been reported that when tetracyclines are applied to the cornea, they do not penetrate the intact normal cornea even though they are able to diffuse into spinal fluid and into ocular fluids if the systemic dose is high enough (Douvas MG, et al, Arch Opthalmol. 46:57, 1951).

SUMMARY OF THE INVENTION

This invention provides a method of treating an ocular infection, comprising topically administering, to an eye of an animal, including man, in need of such treatment, an ocular infection-treating amount of azithromycin. Topical administration means the application, directly to the surface of an eye, of azithromycin in a composition comprising azithromycin and a pharmaceutically acceptable topical carrier. In a preferred embodiment, the composition is applied directly to an eye as a single dose (equivalent to approximately 5 mg) per day for five days. It is noted that a "single dose" means the amount for a single eye.

The invention further provides pharmaceutical compositions for topical application directly to an eye of an animal, including a human, said compositions being suitable for the treatment of an ocular infection, comprising azithromycin and a pharmaceutical vehicle suitable for topical application, wherein said azithromycin is at a concentration in said vehicle sufficient to remediate said ocular infection. In a preferred embodiment, the concentration of azithromycin in the vehicle is such that a single dose (approx. 5 mg per eye) of said composition administered once daily for five days remediates the infection. The capability of achieving once-a-day topical dosing with azithromycin was highly unexpected considering that most drugs are rapidly cleared from the precorneal area by tear drainage. Thus, commonly most topical regimens using known antibiotics such as gentamycin and erythromycin must be administered frequently with application rates of 4–6 times daily sometimes being required to produce effective drug levels in target ocular tissues. Topical formulations of azithromycin, by contrast, achieve relatively high and sustained levels in ocular tissues including cornea, conjunctiva, lids, and sclera. Because of the excellent penetration of azithromycin into ocular tissues, patient compliance is expected to be significantly enhanced by virtue of this invention.

The types of ocular infections treatable through the topical administration of azithromycin broadly include any eye infection caused by a bacterial species known to be amenable to systemic treatment with azithromycin. In particular, the invention is applicable to the treatment of trachoma, a chronic follicular conjunctivitis due to *Chlamydia trachomatis*, the world's leading cause of preventable blindness.

DETAILED DESCRIPTION

The term "azithromycin" includes the pharmaceutically acceptable salts thereof, and anhydrous as well as hydrated forms. The azithromycin is preferably present as the dihydrate, disclosed, for example, in published European Patent Application 0 298 650 A2 and in co-pending U.S. application Ser. No. 07/994,040 filed Dec. 21, 1992, each of which is herein incorporated by reference.

Compositions (sometimes referred to herein as "formulations") according to the invention comprise azithromycin and a pharmaceutically acceptable vehicle suitable for topical application to an eye. Azithromycin (calculated using the dihydrate) is typically present in the composition at a concentration of 0.1 to 2.5 weight % (w/w), usually 0.2 to 2.0 weight %, based on the weight of the composition. A preferred concentration is 0.5 weight %.

The compositions can include a preservative if desired, although preferred compositions do not contain a preservative. The compositions can also optionally contain surfactants, viscosity enhancers, buffers, sodium chloride, and water to form aqueous sterile ophthalmic solutions and suspensions. In order to prepare sterile ophthalmic ointment formulations, azithromycin is combined with an appropriate vehicle such as mineral oil, liquid lanolin, or white petrolatum. Sterile ophthalmic gel formulations containing azithromycin can be prepared by suspending azithromycin in a hydrophilic base prepared from a combination of, for example, a carboxyvinyl polymer sold under the designation Carbopol® (registered trademark of the B. F. Goodrich Company for a series of such polymers) according to published formulations for analogous ophthalmic preparations. Tonicity agents may also be incorporated in such gel formulations.

Azthromycin can be formulated as an ophthalmic solution in isotonic saline using glycerine as an isotonicity agent. A preservative can optionally be included as an excipient. Such ophthalmic solutions also include a pharmaceutically acceptable buffering agent, typically a combination of boric acid and sodium borate, sufficient to maintain the pH of the solution between 7 and 8.

A preferred composition is 0.5% w/w azithromycin dihydrate suspended in an inert, non-allergenic, preservative-free vehicle consisting of white petrolatum (55% w/w), mineral oil (42.5% w/w), and lanolin (2% w/w).

The invention is further disclosed by means of the following non-limiting examples. In the examples, reference to "water" means sterile water, suitable for use as water for injection.

EXAMPLE 1

A preferred embodiment was prepared by incorporating 5 g of azithromycin dihydrate into 995 g of a sterile vehicle comprising 55% by weight of petrolatum, 43% by weight of light mineral oil, and 2% by weight of lanolin. The procedure involved first heating an excess amount of the ointment vehicle of the aforementioned composition to 70° C. in a glass vessel to produce a melt. In the next step, 995 g of the molten sterile ointment was transferred into a compounding vessel equipped with a mixer and 5 g of the azithromycin hydrate was added to the melt under agitation at 70° C. to form a suspension. The azithromycin containing ointment was rapidly cooled by placing the compounding vessel in an ice bath. The "0.5% azithromycin ointment" was then filled into 1 cc unit dose plastic syringes for dose application. This ointment may be sterilized by gamma radiation using a cobalt-60 source.

EXAMPLE 2

A 0.5 weight percent azithromycin dihydrate opthalmic solution is prepared by dissolving 50 g of azithromycin dihydrate (0.5 weight %), 67.0 g (0.67 weight percent) boric acid, 20.7 g (0.207 weight percent) sodium borate decahydrate, 100 g (1.0 weight percent) glycerin, 100 g of polyethylene glycol 300 (1.0 weight percent), and 0.40 g (0.004 weight percent) thimerosal (as a preservative) in about 8000 g of deionized distilled water. The pH is adjusted to 7.2 with HCl and NaOH. The final batch weight is brought to 10,000 g with the addition of the required amount of water. The final solution is filtered through a 0.2 micron Millipore filter and filtered into vials.

EXAMPLE 3

In a preferred embodiment, an approximate 0.5 weight percent azithromycin dihyrate opthalmic suspension is prepared as follows: 600 g of petrolatum is heated to 90° C. for 2 hours in a jacketed 316 stainless steel vessel. The temperature is then decreased to 60° C. Light mineral oil, 350 g, is added to the petrolatum under mild agitation. The solution is passed through a sintered glass filter. Azithromycin dihyrate, 5 g, is dispersed into the mineral oil/petrolatum solution under agitation to form a finely dispersed suspension. The suspension is cooled under slow agitation to form a semisolid suspension. The suspension is filled into plastic, polypropylene tubes and sterilized by gamma radiation using a cobalt-60 source.

EXAMPLE 4

A 0.5 weight percent azithromycin dihyrate opthalmic suspension is prepared as follows: 600 g of PEG 4000 is heated to 90° C. for 2 hours in a jacketed 316 stainless steel vessel. The temperature is brought down to 60° C. PEG 400, 350 g, is added to the petrolatum under mild agitation. The solution is passed through a sintered glass filter. Azithromycin dihyrate, 50 g, is dispersed into the PEG 4000/PEG 400 solution under agitation to form a finely dispersed suspension. The suspension is cooled under slow agitation to form a semisolid suspension. The suspension is filled into plastic, polypropylene tubes and sterilized by gamma radiation using a cobalt-60 source.

|  | % w/w |
| --- | --- |
| Azithromycin Dihydrate | 3.50 |
| Chlorbutol BP | 0.50 |
| Carbopol ® 934P | 2.50 |
| NaOH (4% w/v solution) | 6.21 |
| Water | 87.29 |

Azithromycin dihydrate is dispersed in the sterile unneutralised Carbopol in water containing chlorbutol BP in solution. A sterile 4% w/v sodium hydroxide solution is then added with constant mixing to a final pH of 4–6.

EXAMPLE 6

|  | % w/w |
| --- | --- |
| Azithromycin Dihydrate | 3.50 |
| Chlorbutol BP | 0.50 |
| Citric acid monohydrate** | 0.117 |
| Sodium citrate dihydrate** | 0.112 |
| Sodium citrate 1% solution** | qs |
| Hydroxypropylmethylcellulose 2906 USP 4000 cps (sterile) | 3.80 |
| Water | to 100.00 |

**buffers

Citric acid, sodium citrate and chlorbutol BP are dissolved in 95% of the total water and the solution sterilized. Azithromycin powder is dispersed in the solution at ambient temperature using a high shear mixer. The hydroxypropylmethylcellulose, previously sterilized, is dispersed in the suspension and then allowed to hydrate over a period of about 15 minutes. The pH is adjusted to between 46 with a 1% solution of sterilized sodium citrate. The gel is adjusted to final weight with water and mixed thoroughly.

EXAMPLE 7

The following suspension, gelling in situ at body temperature, is prepared:

|  | % w/w |
| --- | --- |
| Azithromycin Dihydrate | 3.50 |
| benzalkonium chloride BP | 0.02 |
| citric acid monohydrate | 0.117 |
| sodium citrate dihydrate | 0.112 |
| Pluronic ® F127** | 19.00 |
| sodium citrate/citric acid solution | qs |
| water | to 100.00 |

**Pluronic ® F127 is a polyoxyethylene-polyoxpropylene block copolymer of average molecular weight about 11,500

Citric acid, sodium citrate and benzalkonium chloride are dissolved in 98% of the total water. The Pluronic® F127 is dispersed in this solution and left to hydrate overnight. The preparation is then thoroughly mixed and the pH adjusted to 4–6 with sodium citrate or citric acid solution as appropriate. The solution is made to 96.5% of the total weight and sterile filtered into a sterile container. Azithromycin is dispersed aseptically in the filtered solution using a high shear mixer.

EXAMPLE 8

The following gel is prepared under strictly aseptic conditions:

|  | % w/w |
| --- | --- |
| Azithromycin Dihydrate | 3.50 |
| chlorbutol BP | 0.50 |
| ethylene maleic anhydride resin (EMA) type 91 (sterile) | 0.80 |
| dilute ammonium hydroxide solution (1.75% NH$_3$) | 4.40 |
| water | 90.80 |

The sterile EMA resin is dispersed in 50% of the total water, dilute ammonium hydroxide solution is stirred in and the mixture is heated at 95° C. for 15 minutes. The resultant gel is allowed to cool to below 60° C.

The chlorbutol BP is dissolved in the remaining 50% of the water, at a temperature not exceeding 60° C., and sterile filtered into the gel which is mixed slowly.

Azithromycin is thoroughly dispersed in the gel.

What is claimed is:

1. A method of treating an ocular infection, comprising topically administering to an eye of an animal in need of such treatment an ocular infection-treating amount of azithromycin.

2. A method as defined in claim 1 wherein said azithromycin is present in a composition comprising a pharmaceutically acceptable topical vehicle at a concentration of from 0.1 to 2.5 weight percent.

3. A method as defined in claim 2, wherein said composition is administered once daily.

4. A method as defined in claim 1, wherein said animal is a human.

5. A method as defined in claim 2, wherein said azithromycin concentration is from 0.2 to 2.0 weight %.

6. A method as defined in claim 5, wherein said azithromycin concentration is 0.5 weight %.

7. A method as defined in claim 1, wherein said azithromycin is in the form of the dihydrate.

8. A method as defined in claim 1, wherein said ocular infection is trachoma.

* * * * *